United States Patent
Tao et al.

(10) Patent No.: US 10,603,218 B2
(45) Date of Patent: Mar. 31, 2020

(54) CHEMICALLY MODIFIED SEACELL FIBRES, WOUND DRESSING MADE THEREFROM AND PREPARATION METHOD THEREOF

(71) Applicant: FOSHAN UNITED MEDICAL TECHNOLOGIES, LTD., Foshan, Guangdong (CN)

(72) Inventors: Bingzhi Tao, Guangdong (CN); Xiaodong Wang, Guangdong (CN)

(73) Assignee: FOSHAN UNITED MEDICAL TECHNOLOGIES, LTD., Foshan (CN)

( * ) Notice: Subject to any disclaimer, the term of this patent is extended or adjusted under 35 U.S.C. 154(b) by 499 days.

(21) Appl. No.: 14/655,849

(22) PCT Filed: Sep. 2, 2013

(86) PCT No.: PCT/CN2013/082802
§ 371 (c)(1),
(2) Date: Jun. 26, 2015

(87) PCT Pub. No.: WO2014/101458
PCT Pub. Date: Jul. 3, 2014

(65) Prior Publication Data
US 2015/0335492 A1   Nov. 26, 2015

(30) Foreign Application Priority Data
Dec. 28, 2012 (CN) .......................... 2012 1 0586749

(51) Int. Cl.
| | | |
|---|---|---|
| *A61F 13/00* | (2006.01) | |
| *D06M 11/38* | (2006.01) | |
| *A61L 15/28* | (2006.01) | |
| *A61L 15/60* | (2006.01) | |
| *D06M 13/21* | (2006.01) | |
| *D01C 3/00* | (2006.01) | |
| *D06M 16/00* | (2006.01) | |
| *D06M 101/06* | (2006.01) | |

(52) U.S. Cl.
CPC .. *A61F 13/00012* (2013.01); *A61F 13/00008* (2013.01); *A61F 13/00042* (2013.01); *A61F 13/00063* (2013.01); *A61F 13/00068* (2013.01); *A61L 15/28* (2013.01); *A61L 15/60* (2013.01); *D01C 3/00* (2013.01); *D06M 11/38* (2013.01); *D06M 13/21* (2013.01); *D06M 16/00* (2013.01); *A61F 2013/0017* (2013.01); *D06M 2101/06* (2013.01); *Y10T 428/2927* (2015.01); *Y10T 428/2929* (2015.01)

(58) Field of Classification Search
None
See application file for complete search history.

(56) References Cited

U.S. PATENT DOCUMENTS

| | | | | |
|---|---|---|---|---|
| 6,080,420 A | * | 6/2000 | Qin ................. | A61L 15/225 424/443 |
| 2003/0105419 A1 | * | 6/2003 | Edwards .......... | A61L 15/28 602/41 |
| 2003/0153860 A1 | * | 8/2003 | Nielsen ........... | A61F 13/0203 602/43 |
| 2003/0180346 A1 | * | 9/2003 | Woods ............. | A61L 15/18 424/446 |
| 2005/0035057 A1 | * | 2/2005 | Zikeli .............. | A24D 3/10 210/602 |
| 2005/0101900 A1 | * | 5/2005 | Qin ................. | A61L 15/18 602/49 |
| 2010/0144669 A1 | * | 6/2010 | Kershaw .......... | A61K 31/717 514/57 |
| 2016/0114074 A1 | * | 4/2016 | Law ................ | A61L 15/28 442/414 |

FOREIGN PATENT DOCUMENTS

CN             101967698 B  *  3/2012

* cited by examiner

*Primary Examiner* — Kim M Lewis
(74) *Attorney, Agent, or Firm* — Matthias Scholl P.C.; Matthias Scholl

(57) ABSTRACT

A chemically modified cellulose/alginate co-spun (seacell) fiber, a wound dressing made therefrom and a preparation method thereof. The seacell fiber is subject to a chemical modification through which a hydrophilic carboxymethyl group is introduced into the cellulose structure making the chemically modified seacell fiber more absorbent. The modified cellulose has a degree of substitution of 0.05-0.5; the seacell fiber has a linear density of 0.5-5 dtex and a fiber length of 5-180 mm. The seacell fiber has hygroscopic and gel-forming properties, while retaining its active ingredient of algae particles.

13 Claims, No Drawings

CHEMICALLY MODIFIED SEACELL FIBRES, WOUND DRESSING MADE THEREFROM AND PREPARATION METHOD THEREOF

FIELD OF THE INVENTION

This invention relates to a chemical modification of cellulose/alginate co-spun fibres and its applications as a medical dressing.

BACKGROUND OF THE INVENTION

It is well known that a moist environment helps the wound healing process by facilitating the interaction between cells and cell proliferation. Chemically modified cellulose, either by carboxymethylation or carboxyethylation, can enhance the properties of cellulose fibres such as the absorbency and gelling ability. Such a material can absorb as much as 15 times of liquid of its own weight. The chemically modified cellulose fibres can form gels on absorption of aqueous solutions to retain the moisture within the material, providing an ideal environment for wound healing and debridement. Furthermore, the gelled dressing can protect the wound by forming a semi-occlusive environment for the wound from the invasion of harmful substances. The chemically modified cellulose also expands on absorbing the fluid, creating a light pressure to the wound bed which would help blood circulation, supply of nutrients and removal the wastes.

Seacell fibres are essentially cellulose/alginate co-spun fibres, made by co-spinning cellulose and alginate through a solvent spun process. The majority of the fibres are cellulose but have alginate particles embedded in the fibres structure. It is a novel re-generated fibre, combining the benefits of both cellulose and alginate. The fibres can provide protein, amino, fat, cellulose and affluent mineral substance making it ideal for medical applications. Essentially, the Seacell fibres are made from the manufacturing procedure of Lyocell fibres, where the finely grinded alginate powder is blended into the cellulose spinning solution. In particular the alginate powder is grinded to fine particles of less than 9 μm, and then transferred to the cellulose NMMO solution. Alternatively, the alginate powder can be introduced into the spinning solution before cellulose dissolution, with a spinning solution composed of cellulose, alginate, NMMO and water. The solution is then extruded into fibres through a wet spinning process. The seacell shares the similar properties with that of the Lyocell fibres, such as tensile strength, processability etc. Through electron microscopy, it can be seen that seacell fibres have a porous structure, with some horizontal orientation and low crystallization. It has been found that the properties of the alginate component in the finished fibres are maintained, allowing some ingredients of the alginate to be released through the porous structure of the fibres in a moist environment.

Compared with Lyocel fibres, the seacell fibres have the added alginate component which binds metal ions. Additionally, alginate particles contain some minerals which help skin regeneration. It also contains some antibacterial ingredients providing some protection to the skin.

CN101967698A describes the manufacturing method of alginate/cellulose co-spun fibres, which includes the following steps: (1) the cellulose pulp is placed into NaOH solution to get alkalized cellulose; (2) sodium alginate is introduced into alkalized cellulose, with a percentage of up to 1~5% by weight; (3) $CS_2$ is introduced into the above mixtures to start the reaction, and then dissolved by deionized water to attain cellulose/alginate xanthate viscose solution; (4) the spinning solution is made by filtration and deaeration of the cellulose/alginate xanthate viscose solution; (5) the said spinning solution is extruded to attain cellulose/alginate con-spun fibres; (6) after stretching and other further processing the cellulose/alginate co-spun fibres are made.

CN 101613893A describes the manufacturing method of bacterial cellulose/alginate co-spun fibres. The sodium alginate powder is placed into the bacterial cellulose solution with ultrasonic dispersion. The solution is then extruded through a wet spinning process to make the bacterial cellulose/alginate co-spun fibres. The fibres contain 5-20% by weight of sodium alginate and 80-95% of bacterial cellulose. The manufacturing method also includes dissolving bacterial cellulose into an imidazole chloride salt ionic solution at a concentration of 5~10% by weight; followed by adding some fine sodium alginate powder into the above solution. After dispersion and deaeration, the said solution is extruded into a coagulant bath, dried and stretched to obtain the bacterial cellulose/alginate co-spun fibres.

CN101168869A describes a soy protein/alginate/cellulose fibre, as well as its manufacturing method. The spinning solution consists of soy protein, alginate and a high viscosity cellulose solution. The protein/alginate/cellulose co-spun fibres are obtained after multi-step coagulation process. The finished fibres contain 15-60% by weight of soy protein, 3-8% by weight of alginate and 32-82% of cellulose.

However, the above technology has obvious weakness, such as the particle size of alginate powder being too big, the dispersion of alginate powder not being very uniform and the independent relationship between the each component. Moreover, the finished fibre does not have sufficient absorbency and gelling ability which makes the fibre less ideal for being materials for wound dressings.

SUMMARY OF THE INVENTION

In order to address the above weakness, this invention provides chemically modified seacell fibres, a wound dressing made of the chemically modified seacell fibres and its manufacturing method. The seacell fibres refer to cellulose/alginate co-spun fibres made from a solvent (wet) spinning process. During the chemical modification process, a hydrophilic group is conducted to seacell's cellulose component. Therefore the wound dressing made from the said chemically modified cellulose/alginate co-spun fibre can provide the benefits of both alginate and chemically modified cellulose, i.e. calcium and other nutrition from the alginate and gelling and absorbency from the chemically modified cellulose.

The first aspect of the present invention is to provide a chemically modified cellulose/alginate co-spun fibre. After the chemical modification, hydrophilic groups are introduced to the cellulose of the said fibres. The modified cellulose of the said chemically modified cellulose/alginate co-spun fibres has a degree of substitution of 0.05-0.5, preferably 0.2-0.4. The linear density of the said chemically modified cellulose/alginate co-spun fibres is 0.5 to 5 dtex, preferably 2 to 4 dtex. The fibre length is 5 to 180 mm, preferably 15-125 mm.

The seacell fibre of the present invention is made by adding alginate particles into the cellulose spinning solution followed by wet spinning process or solvent spinning operation.

The diameter of the said alginate particle is between 1 to 100 μm, preferably 1 to 50 μm.

The said alginate particle selects from red algae, brown algae and other algae.

The said alginate particles are dispersed into the cellulose spinning solution uniformly. The said chemically modified cellulose is carboxymethyl cellulose or carboxyethyl cellulose.

The chemically modified cellulose in the present invention can absorb wound exudates and form a gel, which facilitates the release of the active material of alginate, and provides a moist and nourish environment for the wound healing process.

The said nourishing materials are alginate acid, organic, ammonia acid, mineral, fat and vitamin.

The said alginate in the present invention is a high mannuronic acid, or high guluronic acid or mixture of both.

The second aspect of the present invention concerns a wound dressing comprising the said chemically modified cellulose/alginate co-spun fibres, or the blend of the said chemically modified cellulose/alginate co-spun fibres and other fibres. The said wound dressing has an absorption capacity of 12 g/100 cm2 or above to solution A. Solution A contains 8.298 g sodium chloride and 0.368 g anhydrous calcium chloride per 1 liter pure water.

Wet strength is an important indicator for the wound dressing. The said wound dressing has a wet strength of 0.3 N/cm or above. Due to the fact that such a dressing will become weak and heavy after absorbing wound exudates or solution A and form a gel, the testing for wet strength is very difficult. The sample will be damaged and break if the force to clamp the sample is too big, or will become too slippery if the force is too small. Therefore only the middle part of the sample is wet during the wet strength test. The basic procedure for wet strength testing is described as follows:

1) The first specimen is cut into 2 cm×7 cm. The second specimen can be cut, take a 10×10 cm dressing as the example at the perpendicular position to the first piece so that one of the specimen is for MD (machine direction) and the other for CD (cross machine direction).

2) Fold the specimen and place the middle part pf the specimen into the solution for 30 seconds. It is recommended to use solution A as described in BP1995;

3) Place the above specimen into the two clamps of the Tensile Tester;

4) The distance between the clamps is set to 50 mm, and the speed is set at 100 mm/min;

5) Start the Tensile Tester to measure the maximum force to break the sample. It is recommended to test the other samples from the same dressing immediately after so that one of the readings (highest) can be recorded as CD, and the other reading as MD;

6) It is recommended to test at least five samples (5 MD and 5 CD) for wet strength. Take the average value as the wet strength for the sample.

The wound dressing of the present invention can be made of the said chemically modified seacell fibres or of the blend of the said chemically modified seacell fibres and other fibres. The said other fibres can be selected from unmodified seacell fibres, unmodified cellulose, carboxymethyl cellulose fibres, carboxyethyl cellulose fibres, alginate fibres, chitosan fibres, acylated chitosan fibres, carboxymethyl chitosan fibres, lyocel fibres, viscose fibres, polyamide fibres, PVA fibres and polyester fibres.

The wound dressing in the present invention can also contain antibacterial agents, for example silver salt, nano silver and PHMB.

The said dressing can be manufactured by weaving, knitting and nonwoven process.

The present invention also provides a method of manufacturing chemically modified seacell fibres, including the following steps:

1) Completely immerse cellulose/alginate co-spun (seacell) fibres into the sodium hydroxide solution with a concentration of 10% to 50% at room temperature. The volume ratio between seacell fibres and sodium hydroxide is from 1:7 to 1:10;

2) Take the fibres out of the solution and squeeze the fibres, and place the fibres into the reacting solution for 10 to 120 minutes. The said reacting solution is made up of sodium chloroacetate, sodium hydroxide, water and ethanol, and the concentration of sodium chloroacetate is between 18-50% by weight;

3) The fibres are placed into the acid solution for washing twice, and then into the ethanol washing solution containing 0.1% to 5% tween 20. The said acid solution consists of 0.5-5% acetic acid, 20-60% water and 35-79.5% ethanol, and the mass ratio between acid solution and fibres are within 5:1 to 50:1;

4) After washing, the fibres are dried for 10-60 minutes at 30-80° C.

The reacting in above step 2 shall be carried out as the following: firstly, the solution shall be heated to 30-50° C., and then the fibres from step 1) are placed into the reacting solution. Continue to heat until the solution temperature reaches 40-65° C., then maintain the temperature until a satisfactory gelling is achieved.

In conclusion, the present invention provides a manufacturing method to obtain the chemically modified cellulose/alginate co-spun fibres which is absorbent and gelling. The modification enhances the property of the chemically modified cellulose/alginate co-spun (seacell) fibres, providing ideal material for the advanced wound dressing.

When the said wound dressing is used to manage chronic wounds, the dressing absorbs the exudates and forms gels, providing a moist environment for the healing process. As alginate particle is contained in the cellulose structure, it provides the advantages of cellulose fibres such as strength and softness, also the benefits of alginate such as being bacteriostatic, and providing calcium and nutrition. After chemical modification by introducing hydrophilic groups, such as carboxymethylation or carboxyethylation, the fibres become absorbent and gelling; ideal for the management of moderate or heavy exudates wounds. Additionally, the alginate component of the said chemically modified cellulose/alginate co-spun fibres provides a slow release of nutritious and antibacterial agents, this is very helpful for the slow wound healing process.

More importantly, the performance and the distribution of the alginate particle is not affected by the process of chemical modification. The combination of absorbency and gelling of chemically modified cellulose and availability of alginate particles makes the fibres ideal for wound dressing and enhances the application of the seacell fibres.

DETAILED DESCRIPTION OF THE PREFERRED EMBODIMENTS

Example 1

(1) 200 g of cellulose/alginate co-spun fibres (purchased from Smartfibres) is placed into 1000 ml 18% by weight of sodium hydroxide for 60 minutes;

(2) The above fibres are taken out of the solution and squeezed, and then immersed into the reacting solution which has been preheated to 41° C. The fibres are kept in the solution for 60 minutes at 50-55° C. The said reacting solution consists of 1000 g sodium chloroacetate, 830 g 30% sodium hydroxide solution, 2000 g ethanol and 2000 g deionized water;

(3) Take the fibres out of the reaction solution, and then place it into the acid solution for washing for 30 minutes. The fibres are washed twice in the solution until its pH value become neutral or a slightly acidic. The said acid solution consists of 500 ml ethanol, 300 ml pure water and 200 ml acid acetic;

(4) Take the fibres out of the washing solution, squeeze and then place it into the washing solution containing the 1000 ml ethanol and 2% by weight of Tween 20;

(5) Place the fibres in the oven and dry out the fibres.

The degree of substitution of the above chemically modified cellulose/alginate co-spun fibres is 0.29.

The linear density of the above cellulose/alginate co-spun fibres is 3 dtex, and the staple length is 50 mm. The above chemically modified cellulose/alginate co-spun fibres are converted into nonwoven pads by a carding and needle punching process. After slitting, cutting, packaging and sterilization, the dressing's absorbency and wet strength is measured as 19 g/100 cm$^2$ and 0.35 N/cm respectively.

Example 2

(1) At room temperature, 100 g cellulose/alginate co-spun fibres (purchased from Smartfibres) are placed into 600 ml 25% by weight sodium hydroxide solution for 50 minutes;

(2) The above fibers are taken out from the solution and squeezed to remove excessive solution. The fibres are then immersed into the reacting solution which has been pre-heated to 38° C. The fibres are kept in the solution for 60 minutes at 50-60° C. The said reacting solution consists of 1000 g sodium chloroacetate, 1630 g 30% sodium hydroxide solution, 2500 g ethanol and 1450 g deionized water;

(3) The fibres are taken out of reaction solution, and then placed them into the acid solution for washing for 30 minutes. Repeat the washing twice in this solution until its pH value become neutral or a slightly acidic. The said acid solution consists of 500 ml ethanol, 300 ml pure water and 200 ml acid acetic;

(4) Take the fibres out of the washing solution, squeeze and then place it into the washing solution containing the 600 ml ethanol and 1.5% by weight of Tween 20;

(5) Place the fibres in the oven and dry out the fibres.

The degree of substitution of the above chemically modified cellulose/alginate co-spun fibres is 0.28.

The linear density of the above cellulose/alginate co-spun fibres is 4 dtex, and the staple length is 60 mm. The above chemically modified cellulose/alginate co-spun fibres are converted into nonwoven pads by a carding and needle punching process. After slitting, cutting, packaging and sterilization, the dressing's absorbency and wet strength are measured as 19.5 g/100 cm$^2$ and 0.40 N/cm respectively.

Example 3

(1) At room temperature, 100 g cellulose/alginate co-spun fibres (purchased from Smartfibres) are placed into 600 ml 25% by weight sodium hydroxide solution for 60 minutes;

(2) The above fibers are taken out from the solution and squeezed to remove excessive solution. The fibres are then immersed into the reacting solution which has been pre-heated to 43° C. The fibres are kept in the solution for 46 minutes at 50-55° C. The said reacting solution consists of 1000 g sodium chloroacetate, 2500 g 30% sodium hydroxide solution, 2500 g ethanol and 1750 g deionized water;

(3) The fibres are taken out of reaction solution, and then placed them into the acid solution for washing for 60 minutes. Repeat the washing twice in this solution until its pH value become neutral or a slightly acidic. The said acid solution consists of 500 ml ethanol, 300 ml pure water and 200 ml acid acetic;

(4) Take the fibres out of the washing solution, squeeze and then place it into the washing solution containing the 600 ml ethanol and 1.5% by weight of Tween 20;

(5) Place the fibres in the oven and dry out the fibres.

The degree of substitution of the above chemically modified cellulose/alginate co-spun fibres is 0.30.

The linear density of the above cellulose/alginate co-spun fibres is 5 dtex, and the staple length is 50 mm. The above chemically modified cellulose/alginate co-spun fibres are converted into nonwoven pads by a carding and needle punching process. After slitting, cutting, packaging and sterilization, the dressing's absorbency and wet strength are measured as 21 g/100 cm$^2$ and 0.35 N/cm respectively.

Example 4

The chemically modified cellulose/alginate co-spun staple fibres from example 1 and carboxymethyl cellulose manufactured by Foshan United Medical Technologies Ltd are blended together, then processed by opening, carding, cross-lapping, double needling, and then by slitting, cutting, packaging and sterilization. The dressing's absorbency was measure at 19 g/100 cm$^2$, and the wet strength at 0.38 N/cm.

Example 5

The chemically modified cellulose/alginate co-spun staple fibres from example 1 and chitosan fibres purchased from Jifa New Material Ltd are blended together, then processed by opening, carding, cross-lapping, double needling, and then slitting, cutting, packaging and sterilization. The absorbency of the dressing is 15 g/100 cm$^2$, and the wet strength is 0.50 N/cm.

Example 6

The chemically modified cellulose/alginate co-spun staple fibres from example 2 and High M alginate fibres manufactured by Foshan United Medical Technologies Ltd are blended evenly then processed by opening, carding, cross-lapping, double needling, and then by slitting, cutting, packaging and sterilization. The absorbency of the dressing is 14 g/100 cm$^2$, and the wet strength is 1.30 N/cm.

Example 7

The chemically modified cellulose/alginate co-spun staple fibres from example 2 and M/G type alginate fibres manufactured by Foshan United Medical Technologies are blended evenly for the nonwoven process of opening, carding, lapping, double needling, and then by slitting, cutting, packaging and sterilization. The absorbency is 16 g/100 cm$^2$, and the wet strength is 1.60 N/cm.

Example 8

The chemically modified cellulose/alginate co-spun staple fibres from example 1, carboxymethyl cellulose manufactured by Foshan United Medical Technologies and chitosan fibres purchased from Jifa New Material Ltd are blended together, followed by opening, carding, cross-lapping, double needling, and then slitting, cutting, packaging and sterilization. The absorbency of the dressing is measured at 21 g/100 cm², and the wet strength is 0.85 N/cm.

Example 9

Manufacture Silver Chemically Modified Cellulose/alginate Co-spun Staple Fibres:

(1) Prepare 30 g cellulose/alginate co-spun staple fibres using the process conditions in example 2;

(2) Prepare 300 ml silver nitrate water/ethanol solution containing 5% ethanol and 1 g silver nitrate. Ensure that the silver nitrate is completely dissolved into solution;

(3) Pre-heat the silver solution to 40° C., and then immerse the chemically modified cellulose/alginate co-spun staple fibres into the solution for 5 minutes;

(4) Introduce sodium chloride into the silver solution at the molar ratio to silver nitrate of 1:1, converting the silver nitrate into silver chloride;

(5) The silver chemically modified cellulose/alginate co-spun staple fibres are dried and then packed.

The silver content of the said silver fibres is 1.2%.

Example 10

Manufacture Silver Chemically Modified Cellulose/alginate Co-spun Staple Fibres:

(1) Prepare 30 g cellulose/alginate co-spun staple fibres using the process conditions in example 2;

(2) Prepare 300 ml silver nitrate water/ethanol solution containing 5% ethanol and 1 g silver nitrate. Ensure that the silver nitrate is completely dissolved into solution;

(3) Pre-heat the silver solution to 40° C., and then immerse the chemically modified cellulose/alginate co-spun staple fibres into the solution for 5 minutes;

(4) Introduce Sodium hypochlorite into the silver solution at the molar ratio to silver nitrate of 1:1, converting the silver nitrate into silver hypochlorite;

(5) The silver chemically modified cellulose/alginate co-spun staple fibres are dried and then packed.

The silver content of the said silver fibres is 1.0%.

Example 11

The silver chemically modified cellulose/alginate co-spun staple fibres from example 10, were blended evenly with the M/G alginate fibres manufactured by Foshan United Medical Technologies Ltd, then processed by opening, carding, cross-lapping, double needling, and then by slitting, cutting, packaging and sterilization. The absorbency of this dressing is 14 g/100 cm², and wet strength is 1.45 N/cm.

Example 12

The silver chemically modified cellulose/alginate co-spun staple fibres from example 10, was blended evenly with acylated chitosan fibres purchased from Jifa New Material Ltd, then processed by opening, carding, cross-lapping, double needling, and then by slitting, cutting, packaging and sterilization. The absorbency of this dressing is 17 g/100 cm², and wet strength is 1.0 N/cm.

What is claimed is:

1. The A chemically modified cellulose/alginate co-spun fiber, wherein a cellulose structure of the chemically modified cellulose/alginate co-spun fiber comprises hydrophilic groups;

a degree of substitution of the cellulose structure is 0.05-0.5;

a linear density of the chemically modified cellulose/alginate co-spun fiber is 0.5-5 dtex;

a length of the chemically modified cellulose/alginate co-spun fiber is 5-180 mm;

alginate particles are embedded in the cellulose structure; and the alginate particles disperse in the cellulose structure evenly.

2. The chemically modified cellulose/alginate co-spun fiber according to claim 1, wherein a size of the alginate particles is 1-100 µm.

3. The chemically modified cellulose/alginate co-spun fiber according to claim 1, wherein the alginate particles come from red algae or brown algae.

4. The chemically modified cellulose/alginate co-spun fiber according to claim 1, wherein the chemically modified cellulose/alginate co-spun fiber is carboxymethyl cellulose or carboxyethyl cellulose.

5. The chemically modified cellulose/alginate co-spun fiber according to claim 1, wherein the chemically modified cellulose/alginate co-spun fiber turns to gel when contacting an aqueous solution, facilitating release of an active ingredient in the alginate particles.

6. The chemically modified cellulose/alginate co-spun fiber according to claim 5, wherein the active ingredient released from the alginate particles is alginate acid, amino acid, mineral, fat and vitamin.

7. A wound dressing comprising the chemically modified cellulose/alginate co-spun fiber of claim 1.

8. The wound dressing according to claim 7, wherein an absorbency of the wound dressing to a solution A is equal to or greater than 12 g/100 cm² and the solution A comprises 8.298 g sodium chloride and 0.368 g anhydrous calcium chloride per liter of pure water.

9. The wound dressing according to claim 7, wherein a wet strength of the wound dressing is equal to or greater than 0.3 N/cm.

10. The wound dressing according to claim 7, wherein the wound dressing comprises an antibacterial agent including silver salt or nano silver or polyhexamethylene guanidine (PHMB).

11. The wound dressing according to claim 7, wherein the wound dressing is manufactured through a weaving process, a knitting process or a non-woven process.

12. A method of manufacturing the chemically modified cellulose/alginate co-spun fiber of claim 1, the method comprises:

1) immersing a cellulose/alginate co-spun fiber into a sodium hydroxide solution with a concentration of 10%-50% by weight at room temperature; a weight ratio between the cellulose/alginate co-spun fiber and the sodium hydroxide solution is 1:7 to 1:10;

2) subjecting the cellulose/alginate co-spun fiber from step 1) to a solution of sodium chloroacetate, sodium hydroxide, water and ethanol, and a concentration of the sodium chloroacetate in the solution is between 18-50% by weight;

3) washing the treated fiber in an acidic solution, and then washing the treated fiber in an ethanol solution containing 0.1-5% Tween 20 by weight; wherein the acidic solution contains 0.5-5% acetic acid, 20-60% water and 35-79.5% ethanol by weight; a weight ratio between the acid solution and the treated fiber is 5:1 to 50:1; and 4) drying the washed fiber at 30-80° C. for 10-60 minutes.

13. The method according to claim 12, wherein the step 2) involves: 21) preheating the solution to 30-50° C. before subjecting the cellulose/alginate co-spun fiber to the heated solution; 22) continuing to heat the solution to the temperature of 40-65° C.; and 23) maintaining the temperature at 45-60° C. until the fiber turns into a gel.

* * * * *